(12) United States Patent
Mueller et al.

(10) Patent No.: US 11,957,920 B2
(45) Date of Patent: Apr. 16, 2024

(54) CONNECTION PIN AND FEEDTHROUGH AND PRODUCTION PROCESS FOR A CONNECTION PIN

(71) Applicant: BIOTRONIK SE & Co. KG, Berlin (DE)

(72) Inventors: Teresa Mueller, Erlangen (DE); Thomas Sontheimer, Rosstal (DE); Stefan Eck, Hoechstadt (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/717,635

(22) Filed: Apr. 11, 2022

(65) Prior Publication Data

US 2022/0233870 A1 Jul. 28, 2022

Related U.S. Application Data

(63) Continuation of application No. 16/051,994, filed on Aug. 1, 2018, now abandoned.

(30) Foreign Application Priority Data

Aug. 2, 2017 (EP) .................................... 17184421

(51) Int. Cl.
*A61N 1/375* (2006.01)
*A61N 1/362* (2006.01)
*A61N 1/39* (2006.01)

(52) U.S. Cl.
CPC ........... *A61N 1/3754* (2013.01); *A61N 1/362* (2013.01); *A61N 1/3956* (2013.01)

(58) Field of Classification Search
CPC ..... A61N 1/3754; A61N 1/362; A61N 1/3956
See application file for complete search history.

(56) References Cited

U.S. PATENT DOCUMENTS

| | | | |
|---|---|---|---|
| 5,272,283 A | 12/1993 | Kuzma | |
| 5,525,759 A | 6/1996 | Salzman | |
| 7,145,076 B2 | 12/2006 | Knappen et al. | |
| 7,747,321 B2 | 6/2010 | Fischbach et al. | |
| 8,162,684 B1 | 4/2012 | Sochor | |
| 8,267,708 B1 | 9/2012 | Sochor | |
| 8,816,242 B2* | 8/2014 | McGiboney | B23K 26/32 |
| | | | 219/121.64 |
| 9,065,224 B2 | 6/2015 | Marzano et al. | |
| 9,821,395 B2 | 11/2017 | Kronmueller et al. | |
| 2004/0191621 A1 | 9/2004 | Heller | |
| 2007/0239222 A1* | 10/2007 | Sprain | A61N 1/3754 |
| | | | 607/37 |

(Continued)

FOREIGN PATENT DOCUMENTS

| | | |
|---|---|---|
| EP | 1688160 A2 | 8/2006 |
| EP | 2529790 A1 | 12/2012 |

(Continued)

*Primary Examiner* — Mallika D Fairchild
(74) *Attorney, Agent, or Firm* — Buchanan Ingersoll & Rooney PC

(57) ABSTRACT

A connection pin of a feedthrough of an implantable medical electronic device has a primarily cylindrical pin body and at least one flattened end section. The flattened end section has at least one planar connecting surface formed on it, especially for connection by material bonding of a band-shaped conductor.

17 Claims, 4 Drawing Sheets

(56) References Cited

U.S. PATENT DOCUMENTS

2012/0261183 A1    10/2012   Pretzlaff et al.
2016/0001387 A1    1/2016   Kronmueller et al.
2016/0076568 A1    3/2016   Dilmaghanian et al.
2017/0165494 A1    6/2017   Kronmueller et al.

FOREIGN PATENT DOCUMENTS

EP    2965783 A1   1/2016
EP    3181194 A1   6/2017

* cited by examiner

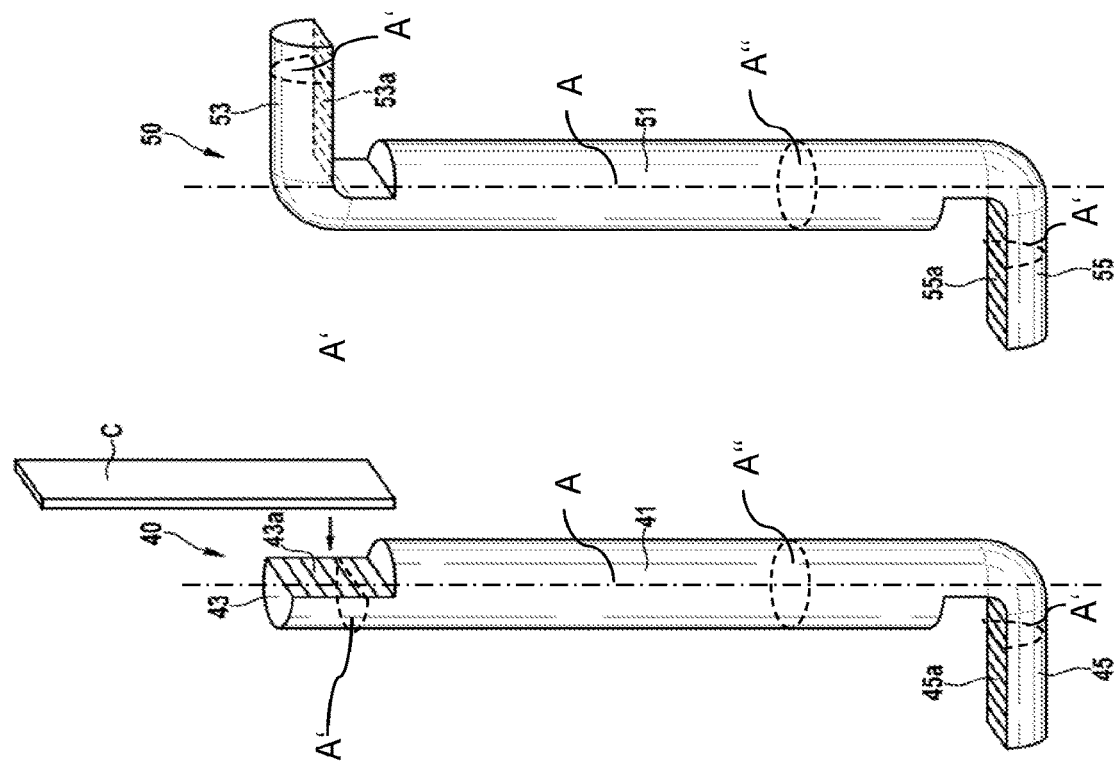

CONNECTION PIN AND FEEDTHROUGH AND PRODUCTION PROCESS FOR A CONNECTION PIN

CROSS-REFERENCE TO RELATED APPLICATION

This application is a continuation application claiming priority to co-pending U.S. application Ser. No. 16/051,994 filed Aug. 1, 2018, which claims the priority, under 35 U.S.C. § 119, of European patent application EP 17184421.0, filed Aug. 2, 2017; the prior applications are herewith incorporated by reference in their entireties.

BACKGROUND OF THE INVENTION

Field of the Invention

The invention relates to a connection pin of a feedthrough of an implantable medical electronic device, a feedthrough comprising such a connection pin, and a method for producing such a connection pin.

Most implantable electromedical devices (IMDs) of practical importance are provided to deliver, through suitably placed electrodes, electrical pulses to excitable body tissue. Furthermore, many devices can selectively measure electrical pulses and stimuli in the body of the patient and record or assess them over a longer period of time to select an individually adapted therapy and to check the success of the treatment in vivo.

To execute these functions, the device has, inside the housing, electronic/electrical functional units for producing and measuring the pulses and for suitable control of the production of pulses, and the device has, on the outside, electrodes directly on it or connections for at least one electrode lead, the distal end section of these connections containing the electrodes for transferring pulses to the tissue. The electronic/electrical functional units inside the device are to be connected with the electrodes or electrode lead connections outside in a way that ensures absolutely and permanently reliable functionality under the special conditions of the implanted state.

The foregoing is accomplished by so-called feedthroughs, which have been the subject of numerous and quite different developments. The task of a feedthrough is to carry the electrical signals through the hermetically sealed housing and in this way to allow the electronics in the hermetically sealed housing to make electrical contact with the electrodes in the body of the patient. In many such feedthroughs, this is done using connection pins that make contact with the printed circuit board or with a similar conductor support located inside the device, and carry the signals through the housing.

U.S. Pat. No. 7,747,321 B2 discloses a cardiac pacemaker 1 as shown in FIG. 1, with a pacemaker housing 3 and a header 5, which has a printed circuit board (PCB) 7 arranged inside it, along with other electronic components, and whose lead connector (not shown) arranged in the header is connected with an electrode lead 9. A feedthrough 11 provided between device housing 3 and header 5 comprises multiple connection pins 13. At one end, the connection pins are inserted through a corresponding hole in the printed circuit board and are soft-soldered with it. They comprise a wire core, made, for instance, of tantalum, niobium, titanium, molybdenum, or copper, and an oxidation-resistant sheath made of a biocompatible material, for instance gold, platinum, titanium, or something similar.

Furthermore, European published patent application EP 3 181 194 A1 discloses a feedthrough comprising connection pins formed out of a shape memory alloy.

Further, European published patent application EP 2 965 783 A1 discloses a method for producing a connection pin for a feedthrough from a semi-finished part comprising at least a second layer element comprising a solder.

In known feedthrough designs, the connection elements are provided by pin band constructions in which a long connection element (pin) penetrates an insulation body of the feedthrough and is used for welding on to a header of the IMD, while a band welded on to the housing-side end of the pin makes the contact with the device electronics (printed circuit board). The pin can consist of materials such as Nb or PtIr and the band can consist of materials such as of Cu or Ni, the pin is hard-soldered in the insulation body, and the band is typically also hard-soldered onto the end of the pin or connected with it through a laser spot weld.

Many medical electronic devices use connection pins that have a so-called nail head, which is made by cold forming a drawn wire material. Typically, the structure of such connection pins is disadvantageously changed as a consequence of cold forming, and the pins frequently show microcracks in their surface. This causes problems with coating, which is necessary for connecting conductors by a soldering process. Furthermore, the surface quality of such connection pins can be affected by drawing grooves, which can, in particular, lead to undesired flowing of connecting solder along the connection pin.

SUMMARY OF THE INVENTION

It is accordingly an object of the invention to provide a connection pin which overcomes a variety of disadvantages associated with the heretofore-known devices and methods of this general type and which provides for a connection pin whose properties are better with regard to connecting a conductor, especially a band-shaped conductor, by means of a connection process involving material bonding. Furthermore, a suitable production process for such a connection pin should be indicated.

With the foregoing and other objects in view there is provided, in accordance with the invention, a connection pin of a feedthrough of an implantable medical electronic device, the connection pin comprising:

an elongated pin body extending along a longitudinal axis of said pin body;

at least one flattened end section integrally connected to said pin body, said at least one flattened end section having a cross-section area that is smaller than a cross-section area of said pin body; and at least one planar connecting surface formed on said at least one flattened end section.

In other words, a connection pin for a feedthrough of an implantable medical electronic device is disclosed, the connection pin comprising: an elongated pin body extending along a longitudinal axis of the pin body; at least one flattened end section that is integrally connected to said pin body, wherein the at least one flattened end section comprises a cross-section area that is smaller than a cross-section area of the pin body; and at least one planar connecting surface formed on the at least one flattened end section.

Particularly, in an embodiment, said cross-section area of the at least one flattened end section extends perpendicular to one of: an extension direction of the at least one flattened end section, the at least one planar connecting surface, the longitudinal axis of the pin body.

Furthermore, in an embodiment, the cross-section area of the pin body extends perpendicular to the longitudinal axis of the pin body.

Particularly, the present invention includes the idea of overcoming certain fundamental disadvantages of connecting the known connection pin by changing the surface geometry, at least in an end section of the pin. The invention further includes the idea of producing in the relevant end section—and only there—a surface geometry that can be optimally fitted to band-shaped connection conductors. Finally, the invention includes the idea of producing, on the pin body, at least one flattened end section on which at least one planar connecting surface is formed, in particular for connection by material bonding of a band-shaped conductor.

Furthermore, according to an embodiment, the pin body is cylindrical.

Further, in an embodiment, the at least one planar connecting surface is configured to be bonded to a band-shaped conductor by way of material bonding.

Furthermore, according to an embodiment, the at least one planar connecting surface is larger than said cross-section area of the pin body.

Further, in an embodiment, the connection pin comprises a further flattened end section opposite the at least one flattened end section, wherein these two end sections are integrally connected to one another by the pin body. Here, both end sections of the connection pin are formed as a flattened end section, respectively, wherein on each flattened end section at least one planar connecting surface is formed. In an embodiment that is an alternative to this, the connection pin comprises a further end section that is formed as a nail head. Here, the further end section/nail head is integrally connected to the at least one flattened end section by the pin body.

Particularly, in an embodiment, the further flattened end section comprises a cross-section area that is smaller than a cross-section area of the pin body. Particularly, in an embodiment, said cross-section area of the further flattened end section extends perpendicular to one of: an extension direction of the further flattened end section, the at least one planar connecting surface of the further flattened end section, the longitudinal axis of the pin body.

Further, in an embodiment, the at least one planar connecting surface of the further flattened end section is larger than said cross-section area of the pin body.

Other embodiments of the invention provide that the at least one flattened end section has two planar connecting surfaces and/or that further flattened end section has two planar connecting surfaces. Here, particularly, the two planar connecting surfaces of the at least one flattened end section or of the further flattened end section form surfaces that face away from each other. This embodiment offers higher design freedom with respect to geometric shape of conductors that are supposed to be connected to the connection pin.

In other embodiments, the at least one flattened end section and/or the further flattened end section is bent at an angle in the range between 30° and 90°, especially at an angle of 90°, with respect to the longitudinal axis of the (e.g. cylindrical) pin body. This bending offers additional degrees of freedom with respect to the shape of the end section of a conductor band to be connected, in particular the shape of the end section of the conductor band that is near the pin, and possibly allows a more compact design of the feedthrough.

In other embodiments, the or every connecting surface (e.g. the at least one planar connecting surface of the at least one flattened end section, or the at least one planar connecting surface of the further flattened end section, or each of said two connecting surfaces of the at least one flattened end section or of the further flattened end section) has a surface structure, especially one oriented essentially transverse to the longitudinal axis or one that is irregular, that prevents a connecting material, which is intended for connection of a band-shaped conductor by material bonding, from running in the direction of the longitudinal axis or towards the pin body. This advantageously makes it possible to compensate, or even overcompensate, for a substantial manufacturing-based disadvantage of connection pins produced from drawn wire.

With the above and other objects in view there is provided, in accordance with the invention, a method for producing a connection pin as detailed above. The method comprising:

providing an annealed wire material; and applying an ultrashort pulse laser treatment to the wire material to form a pin body, at least one flattened end section, and at least one planar connecting surface of the connection pin.

The method aspects of the invention include the idea of producing the connection pin starting from a stress relieved, especially annealed wire material, allowing laser processing methods to be used to produce the inventive end section configuration. The process aspects of the invention also include the idea of producing this end section configuration using an ultrashort pulse laser treatment.

In other words, a method for producing a connection pin according to the present invention is disclosed, the method comprising the steps of: providing an annealed wire material, and applying an ultrashort pulse laser treatment to the wire material to form the pin body, the at least one flattened end section, and the at least one planar connecting surface.

Particularly, also the further flattened end section and the at least one planar connecting surface of the further flattened end section can be formed by applying the ultrashort pulse laser treatment to the wire material. Similarly, said two planar connecting surfaces of the at least one flattened end section or of the further flattened end section can be formed by applying the ultrashort pulse laser treatment.

One embodiment of the process involves forming, particularly in connection with the formation of the respective flattened end section, a surface structure optimized for connection on the at least one planar connecting surface of the at least one flattened end section (or on every connecting surface), preferably doing so by ultrashort pulse laser treatment. This can be done by a surface structure that is deliberately adapted to the joining partner or by a deliberately directed surface roughness.

This contributes both to efficient production of the connection pin with high production yield, and also to a durable contact with long-term stability.

Particularly, such a surface structure can also be formed by ultrashort pulse laser treatment on the at least one planar connecting surface of the further flattened end section.

Furthermore, such a surface structure can also be formed by ultrashort pulse laser treatment on the two opposite planar connecting surfaces of the at least one and/or of the further flattened end section (see also above).

In other embodiments, the connection pin is installed into a feedthrough of an implantable medical electronic device after the at least one flattened end section and/or after the further flattened end section is formed, and the device-internal end section is bent by cold forming in the installed state. This sequence of steps simplifies the realization of feedthroughs with bent connection pins, and under certain circumstances it is the condition that first allows such feedthroughs to be produced. An embodiment of this provides that the device-external end section of the connection pin is bent by cold forming before it is installed into the feedthrough.

At least certain embodiments of the invention allow at least some of the following advantages over known connection pins to be realized:

Increased flexibility is provided in component geometry, material selection, and product applications.

Increased design freedom is provided with respect to the arrangement and geometric configuration of the conductor connections to the device components.

The proposed process can be easily automated and parameterized, and this can be done largely without retooling steps.

It is possible to save the process steps and costs involved in connecting the conductor band by material bonding.

Quality and reliability problems resulting from surface or structure defects in the area of the connecting surfaces are avoided to the greatest possible extent.

Depending on application scenarios, it is possible to do without a multipart pads pin configuration and to realize corresponding savings in production time and costs.

The process security in the step of connecting band-shaped conductors to the contact pin is significantly increased.

Other features which are considered as characteristic for the invention are set forth in the appended claims.

Although the invention is illustrated and described herein as embodied in a connection pin and feedthrough and production process for a connection pin, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 4 is a similar view of a third embodiment of the inventive connection pin;

FIG. 5 is a similar view of a fourth embodiment of the inventive connection pin.

DETAILED DESCRIPTION OF THE INVENTION

Figure 2:
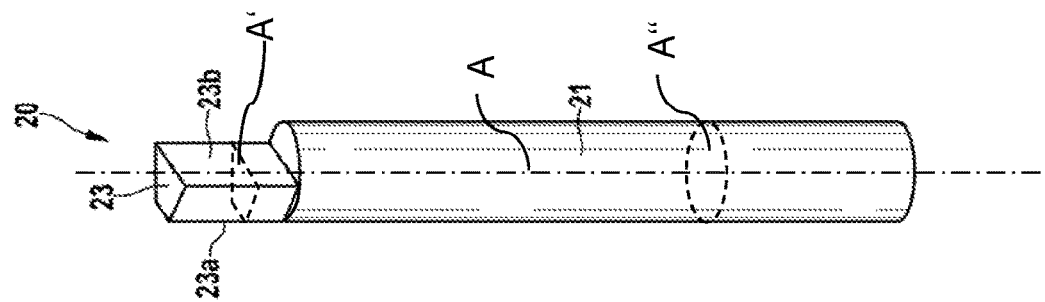
FIG. 2 is a perspective view of first embodiment of the connection pin according to the invention.

Referring now once more to the figures of the drawing in detail and first, particularly, to FIG. 2 thereof, there is shown FIG. 2 is a perspective representation showing a connection pin 20 with a cylindrical pin body 21 extending along a longitudinal axis A. The pin body forms the predominant part of the longitudinal extent of the connection pin. The pin 20 has a, for example prism-shaped end section 23 with two opposite planar connecting surfaces 23a, 23b (i.e. the surfaces 23a, 23b face away from each other) onto which surfaces a conductor band (not shown) can be welded. The geometric configuration of the end section 23 can be imparted by ultrashort pulse laser treatment or possibly also by a mechanical forming step. Furthermore, particularly, the flattened end section 23 comprises a cross-section area A' that is smaller than a cross-section area A" of the pin body 21. The two cross-section areas A', A" extend perpendicular to the longitudinal axis A of the pin body 21. Furthermore, particularly, the connecting surfaces 23a, 23b can each be larger than the cross-section area A" of the pin body 21. Furthermore, the two surfaces 23a, 23b extend parallel to the longitudinal axis A.

Figure 1:
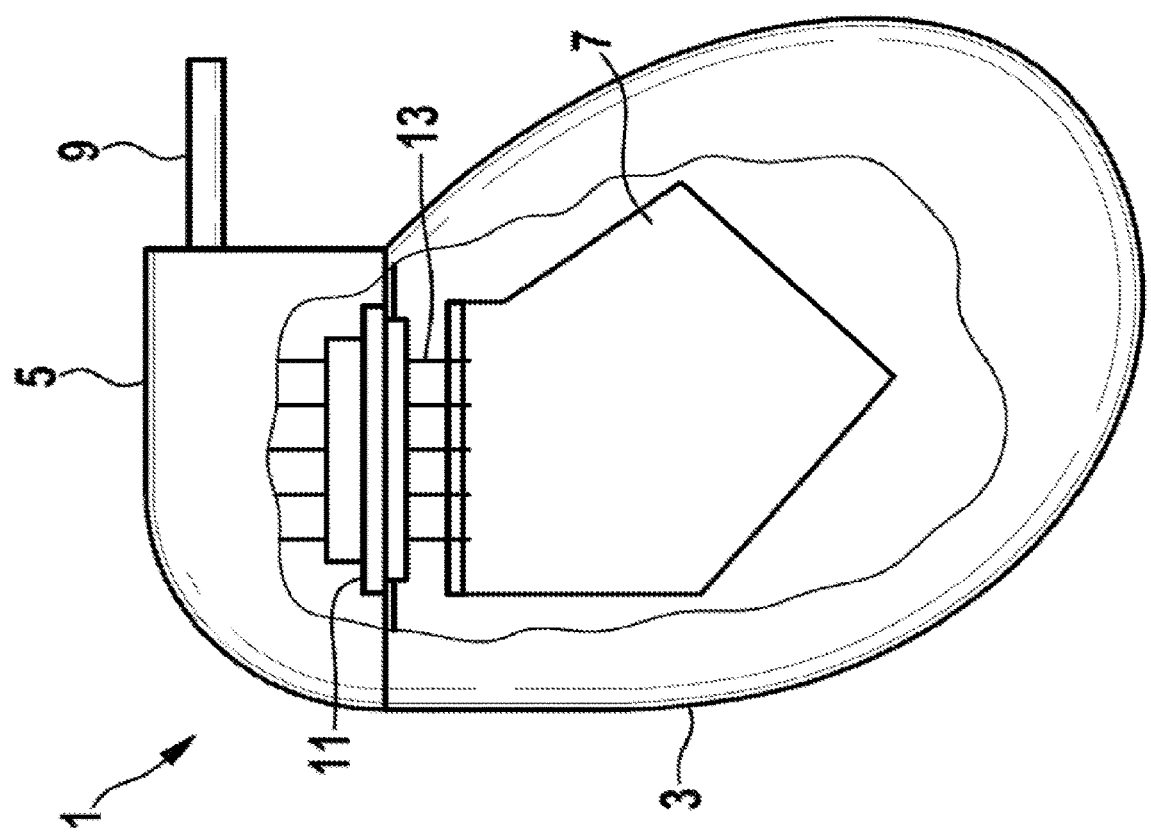
FIG. 1 is a schematic representation of a cardiac pacemaker according to the prior art.
Figure 3:
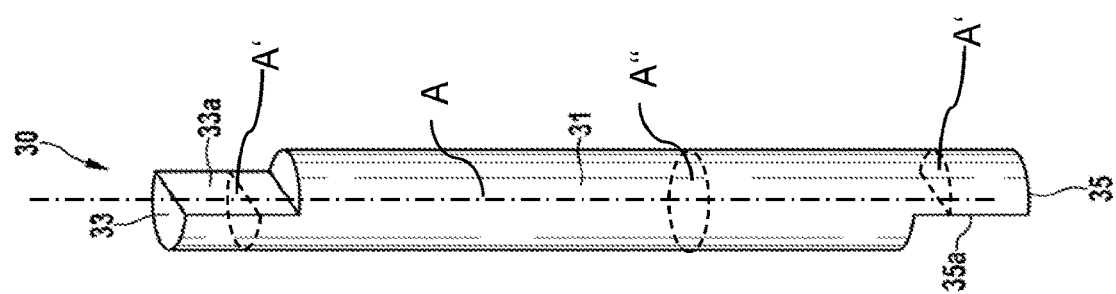
FIG. 3 is a similar view of a second embodiment of the inventive connection pin.

FIG. 3 shows another embodiment of a connection pin 30, which once again has a cylindrical pin body 31 that extends along a longitudinal axis A over most of the longitudinal extension of the connection pin, but whose opposite ends have two deformed flattened end sections 33, 35 formed by e.g. ablation processing (for example, once again by means of an ultrashort pulse laser process). In the end sections 33, 35, the basic cylindrical shape is maintained over most of the cross section, however ablation processing has been used to remove a section of the cylinder, forming, in each case, a planar connecting surface 33a or 35a, to which a conductor band can be welded. The two surfaces 33a, 35a, as illustrated, may face in opposite directions. Further, particularly, each end section 23, 33 comprises a cross-section area A' that is smaller than a cross-section area A" of the pin body 31. The two cross-section areas A', A" extend perpendicular to the longitudinal axis A of the pin body 31. Furthermore, particularly, the connecting surfaces 33a, 35a can each be larger than the cross-section area A" of the pin body 21. Furthermore, the two planar connecting surfaces 33a, 35a extend parallel to the longitudinal axis A.

FIG. 4 shows another embodiment of the invention in which a connection pin 40 once again comprises an essentially cylindrical pin body 41, together with a conductor band C. In this connection pin 40, both end sections 43, 45 are also processed, for instance with an ablation process, to create respective planar connecting surfaces 43a or 45a. Moreover, the connecting surfaces 43a, 45a are structured by microchannels or grooves running transverse to the longitudinal extension/longitudinal axis A of the pin body 41 so as to prevent the running of connecting solder in the longitudinal direction of the connection pin or towards the pin body 41. Moreover, in this embodiment, the end section 45 is bent at right angles to the longitudinal axis A of the pin body 41 of the connection pin. The conductor band C is welded or soldered on to the connecting surface 43a, and the connecting surface 45a can have another conductor band (not shown) attached to it in an analogous fashion (e.g. through a connection by material bonding). Furthermore, particularly, each end section 43, 45 has a cross-section area A' (perpendicular to the respective connecting surface 43a, 45a) that is smaller than a cross-section area A" of the pin body 41 (perpendicular to longitudinal axis A). Furthermore, particularly, the connecting surfaces 43a, 45a can each be larger than the cross-section area A" of the pin body 41.

FIG. 5 shows another embodiment of a connection pin 50 in a configuration which it assumes after installation in a feedthrough (not shown), namely the configuration in which both end sections 53, 55 integrally connected to the pin body 51 are bent at right angles to the longitudinal axis A of the pin body 51. Here the connecting surfaces 53a, 55a can exhibit microroughness, which prevents the flowing of solder material in the longitudinal direction of the connection pin, similar to the embodiment in FIG. 4. Furthermore, particularly, each end section 53, 55 can comprises a cross-section area A' that is smaller than a cross-section area A" of the pin body 51. Furthermore, particularly, the connecting surfaces 53a, 55a can each be larger than the cross-section area A" of the pin body 51.

Figure 6:
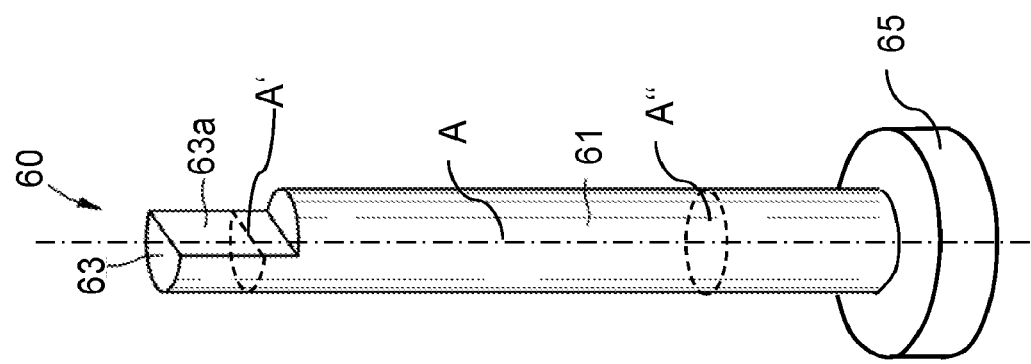
FIG. 6 is a similar view of a fifth embodiment of the inventive connection pin.

Further, FIG. 6 shows a modification of the embodiments shown in FIGS. 2 to 5. Here, one end section of the connection pin 60 forms a nail head 65 that is integrally connected to the pin body 61 that extends along the longitudinal axis A. The flattened end section 63 of the connection pin 60 is formed as shown in FIG. 3, but may also be formed according to one of the other embodiments shown e.g. in FIG. 2, 4, or 5. Particularly, the connecting surface 63a can comprise a surface structure comprising e.g. microchannels or grooves running transverse to the longitudinal extension/longitudinal axis A of the pin body 61 so as to prevent the running of connecting solder in the longitudinal direction of the connection pin or towards the pin body 61. Furthermore, particularly, the flattened end section 63 has a cross-section area A' (perpendicular to longitudinal axis A) that is smaller than a cross-section area A" (perpendicular to longitudinal axis A) of the pin body 61. Furthermore, particularly, the connecting surface 63a can be larger than the cross-section area A" of the pin body 21 and can extend parallel to the longitudinal axis A of the pin body 61.

Many other variants of the embodiments of the invention shown here in the examples and aspects of the invention emphasized further above are possible.

Finally, in the following, further aspects of the present invention and embodiments of these aspects are formulated as enumerated items. These items may also be formulated as claims of the present invention. The reference numerals in parentheses relate to the Figures.

Item 1: A connection pin (20, 30, 40, 50) of a feedthrough (11) of an implantable medical electronic device (1) with an essentially cylindrical pin body (21; 31; 41; 51) and at least one flattened end section (23; 33, 35; 43, 45; 53, 55) that has at least one planar connecting surface (23a, 23b; 33a, 35a; 43a, 45a; 53a, 55a) formed on it, especially for connection by material bonding of a band-shaped conductor (C).

Item 2: A connection pin according to item 1, wherein both ends of the pin body (31; 41; 51) have a flattened end section (33, 35; 43, 45; 53, 55), on which at least one planar connecting surface (33a, 35a; 43a, 45a; 53a, 55a) is formed.

Item 3: A connection pin according to item 1, wherein a nail head is formed on one end of the pin body.

Item 4: A connection pin according to any one of the preceding items, wherein the or every flattened end section (23) has two planar connecting surfaces (23a, 23b), which form, in particular, surfaces of the end section that are opposite one another.

Item 5: A connection pin according to any one of the preceding items, wherein the or one flattened end section (45; 55) is bent at an angle in the range between 30° and 90°, especially at an angle of 90°, with respect to the longitudinal axis of the cylindrical pin body (41; 51).

Item 6: A connection pin according to any one of the preceding items, wherein the or every connecting surface (23a, 23b; 33a, 35a; 43a, 45a; 53a, 55a) has a surface structure, especially one oriented essentially transverse to the longitudinal axis or one that is irregular, that prevents a connecting material, which is intended for connection of a band-shaped conductor (C) by material bonding, from running in the direction of the longitudinal axis.

Item 7: A feedthrough (11) of an implantable medical electronic device, especially a cardiac pacemaker or a cardioverter, that has at least one connection pin according to any one of items 1 through 6.

Item 8: A production process for a connection pin (20, 30, 40, 50) according to any one of items 1 through 6, wherein the pin body (21; 31; 41; 51) is produced from an annealed wire material and undergoes ultrashort pulse laser treatment to form the or every flattened end section (23; 33, 35; 43, 45; 53, 55).

Item 9: A process according to item 8 that involves forming, in connection with the formation of the flattened end section (23; 33, 35; 43, 45; 53, 55), a surface structure that is oriented essentially transverse to the longitudinal axis on the or every connecting surface (23a, 23b; 33a, 35a; 43a, 45a; 53a, 55a), and doing so by ultrashort pulse laser treatment.

Item 10: A process according to item 8 or 9, wherein the connection pin (20, 30, 40, 50, 60) is installed into a feedthrough of an implantable medical electronic device after the or every flattened end section (23; 33, 35; 43, 45; 53, 55) is formed, and the device-internal end section (45; 55) is bent by cold forming in installed state.

Item 11: A process according to item 10, wherein the device-external end section (53) of the connection pin is bent by cold forming before it is installed into the feedthrough.

The invention claimed is:

1. A connection pin of a feedthrough of an implantable medical electronic device, the connection pin comprising:
   an elongated pin body extending along a longitudinal axis of said pin body, said elongated pin body having a first end and a second end;
   a first flattened end section integrally connected to said first end, said first flattened end section having a cross-section area that is smaller than a cross-section area of said pin body;
   a first planar connecting surface formed on said first flattened end section, the first planar connecting surface extending parallel to an extension direction of said first flattened end section;
   a second flattened end section integrally connected to said second end, said second flattened end section having a cross-section area that is smaller than a cross-section area of said pin body; and
   a second planar connecting surface formed on said second flattened end section, the second planar connecting surface extending parallel to an extension direction of said second end.

2. The connection pin according to claim 1, wherein said pin body is cylindrical.

3. The connection pin according to claim 1, wherein said first planar connecting surface and/or said second planar connecting surface is configured to be bonded to a band-shaped conductor by way of material bonding.

4. The connection pin according to claim 1, wherein a sum of surface areas of said first planar connecting surface and said second planar connecting surface is larger than said cross-section area of said pin body.

5. The connection pin according to claim 1, wherein said first end at said first flattened end section is bent at an angle in a range between 30° and 90° with respect to the longitudinal axis of said pin body.

6. The connection pin according to claim 1, wherein:
   said first end at said first flattened end section is bent at an angle in a range between 30° and 90° with respect to the longitudinal axis of said pin body; and/or said second end at said second flattened end section is bent at an angle in a range between 30° and 90° with respect to the longitudinal axis of the pin body.

7. The connection pin according to claim 6, wherein:
said first end at said first flattened end section is bent relative to the longitudinal axis of the pin body an angle of 90°; and/or
said second end at said second flattened end section is bent relative to the longitudinal axis of the pin body an angle of 90°.

8. The connection pin according to claim 1, wherein:
said first planar connecting surface and/or said second planar surface has a surface structure that is configured to prevent a connecting material for connection of a band-shaped conductor by material bonding, from running in a direction of the longitudinal axis of said pin body or towards said pin body; and/or
said first connecting surface and/or said second planar surface has a surface structure that is configured to prevent a connecting material for connection of a band-shaped conductor by material bonding, from running in a direction of the longitudinal axis or towards said pin body.

9. The connection pin according to claim 8, wherein said surface structure is oriented transverse to the longitudinal axis, or wherein said surface structure is an irregular surface structure.

10. A feedthrough of an implantable medical electronic device, comprising at least one connection pin according to claim 1.

11. The feedthrough according to claim 10, wherein the implantable medical electronic device is a cardiac pacemaker or a cardioverter.

12. A method for producing a connection pin, the method comprising:
providing an annealed wire material;
applying an ultrashort pulse laser treatment to the wire material to form a pin body, at least one flattened end section, and at least one planar connecting surface of the connection pin according to claim 1.

13. The method according to claim 12, further comprising:
forming a surface structure on the at least one planar connecting surface of the at least one flattened end section by ultrashort pulse laser treatment, and forming the surface structure to be oriented transverse to a longitudinal axis of the pin body.

14. The method according to claim 12, further comprising installing the connection pin into a feedthrough of an implantable medical electronic device after the at least one flattened end section is formed, and bending a device-internal end section of the connection pin by cold forming in an installed state of the connection pin.

15. The method according to claim 14, which comprises bending a device-external end section of the connection pin by cold forming prior to being installed into the feedthrough.

16. A connection pin of a feedthrough of an implantable medical electronic device, the connection pin comprising:
an elongated pin body extending along a longitudinal axis of said pin body, said elongated pin body having a first end and a second end;
a first flattened end section integrally connected to said pin body, said first flattened end section having a cross-section area that is smaller than a cross-section area of said pin body;
at least one planar connecting surface formed on said first flattened end section, the at least one planar connecting surface extending parallel to an extension direction of the first flattened end section; and
a nail head formed on a second end of said pin body, said second end being located at the opposite end of said first end.

17. An implantable medical electronical device, comprising:
a housing,
a header, and
an electrical feedthrough arranged between the housing and the header, the electrical feedthrough comprising:
a connection pin, the connection pin comprising:
an elongated pin body extending along a longitudinal axis of said pin body, said elongated pin body having a first end and a second end;
a first flattened end section integrally connected to said first end, said first flattened end section having a cross-section area that is smaller than a cross-section area of said pin body; and
a first planar connecting surface formed on said first flattened end section, the first planar connecting surface extending parallel to an extension direction of the first flattened end section, and
a second planar connecting surface formed on a second flattened end section, the second planar connecting surface extending parallel to an extension direction of said second end, or
a nail head formed on said second end of said pin body, said second end being located at the opposite end of said first end.

* * * * *